(12) United States Patent
DiMatteo et al.

(10) Patent No.: US 7,766,959 B2
(45) Date of Patent: Aug. 3, 2010

(54) VARIABLE LENGTH ENDOVASCULAR GRAFT PROSTHESIS ADAPTED TO PREVENT ENDOLEAKS

(75) Inventors: Kristian DiMatteo, Waltham, MA (US); Robert Thistle, Bridgewater, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 1208 days.

(21) Appl. No.: 11/090,522

(22) Filed: Mar. 25, 2005

(65) Prior Publication Data

US 2006/0217796 A1  Sep. 28, 2006

(51) Int. Cl.
*A61F 2/06* (2006.01)
(52) U.S. Cl. .................................... 623/1.16
(58) Field of Classification Search ............... 606/161, 606/157, 191–198; 623/1.13, 1.16, 1.23, 623/1.25
See application file for complete search history.

(56) References Cited

U.S. PATENT DOCUMENTS

| | | | |
|---|---|---|---|
| 4,728,328 A | | 3/1988 | Hughes et al. |
| 5,064,435 A | | 11/1991 | Porter |
| 5,156,620 A | * | 10/1992 | Pigott ........................ 623/1.25 |
| 5,755,770 A | | 5/1998 | Ravenscroft |
| 6,102,940 A | | 8/2000 | Robichon et al. |
| 6,129,756 A | | 10/2000 | Kugler et al. |
| 6,152,956 A | | 11/2000 | Pierce |
| 6,221,102 B1 | | 4/2001 | Baker et al. |
| 6,287,335 B1 | * | 9/2001 | Drasler et al. ............... 623/1.28 |
| 6,303,100 B1 | | 10/2001 | Ricci et al. |
| 6,451,051 B2 | | 9/2002 | Drasler et al. |
| 7,226,474 B2 | * | 6/2007 | Iancea et al. ................ 623/1.13 |
| 2002/0052644 A1 | | 5/2002 | Shaolian et al. |
| 2003/0068296 A1 | | 4/2003 | Ricci et al. |
| 2003/0236567 A1 | | 12/2003 | Elliot |

FOREIGN PATENT DOCUMENTS

| | | |
|---|---|---|
| FR | 1526295 | 5/1968 |
| WO | WO 97/09008 | 3/1997 |
| WO | WO 97/17910 | 5/1997 |
| WO | WO 2004/017867 A1 | 3/2004 |
| WO | WO 2006/028925 A1 | 3/2006 |

OTHER PUBLICATIONS

International Search Report, Application No. PCT/US2006/010652 filed Mar. 24, 2006.
Written Opinion of the International Searching Authority from corresponding PCT Application PCT/US2006/010652 dated Sep. 25, 2007.

* cited by examiner

*Primary Examiner*—Kevin T Truong
(74) *Attorney, Agent, or Firm*—Brooks, Cameron & Huebsch, PLLC

(57) ABSTRACT

A variable length endovascular prosthesis adapted to prevent endoleaks is provided that includes a substantially tubular first graft member having an interior surface, an exterior surface, and a proximal end, and a substantially tubular second graft member slidably engaged coaxially within the first graft member. The prosthesis further includes a substantially tubular fluid-tight connecting member attached at one end to the first graft member and attached at another end to the second graft member. The connecting member is axially compressible and expandable to facilitate engagement of the second graft member within the first graft member while maintaining a seal between the graft members.

12 Claims, 3 Drawing Sheets

VARIABLE LENGTH ENDOVASCULAR GRAFT PROSTHESIS ADAPTED TO PREVENT ENDOLEAKS

BACKGROUND OF THE INVENTION

Endovascular graft prostheses are typically used, for example, in the treatment of abdominal aortic aneurysms (AAAs). Once placed, such prostheses must conform to changing vessel morphology. A prosthesis comprised of modular components which are movable relative to one another may provide for such conformation, but leakage between the modular components must be avoided. Fluid leakage at the connection between modular components is termed in the art as an endoleak.

Endoleaks may result from poor integrity at a connection, either as initially installed or subsequently, when the lumen within which the prosthesis is located shrinks and/or kinks or straightens, frequently resulting in modular component separation and/or leakage.

Accordingly, there remains a need for a flexible, variable length endovascular prosthesis in which endoleaks are avoided.

SUMMARY OF THE INVENTION

A variable length endovascular graft prosthesis is adapted to prevent endoleaks. In one embodiment, the prosthesis includes a substantially tubular first graft member and a substantially tubular second graft member engaged coaxially within the first graft member. A substantially tubular fluid-tight connecting member is attached at one end to the first graft member and attached at another end to the second graft member. The connecting member is axially compressible and expandable to facilitate variable length engagement of the second graft member within the first graft member while maintaining a seal between the graft members. The first and second graft members may include, for example, grafts, stent-grafts, or a combination thereof.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 1A:
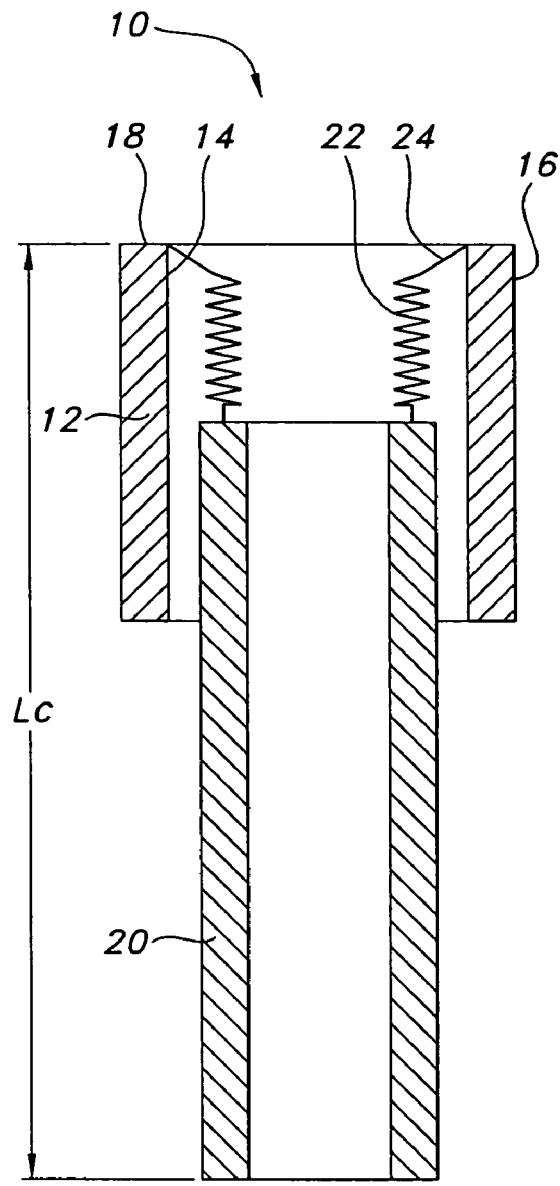
FIG. 1A is a cross-sectional view of an endovascular prosthesis comprised of two coaxially engaged graft members, in a compressed configuration, illustrating a pleated connecting member residing within a first graft member.
Figure 1B:
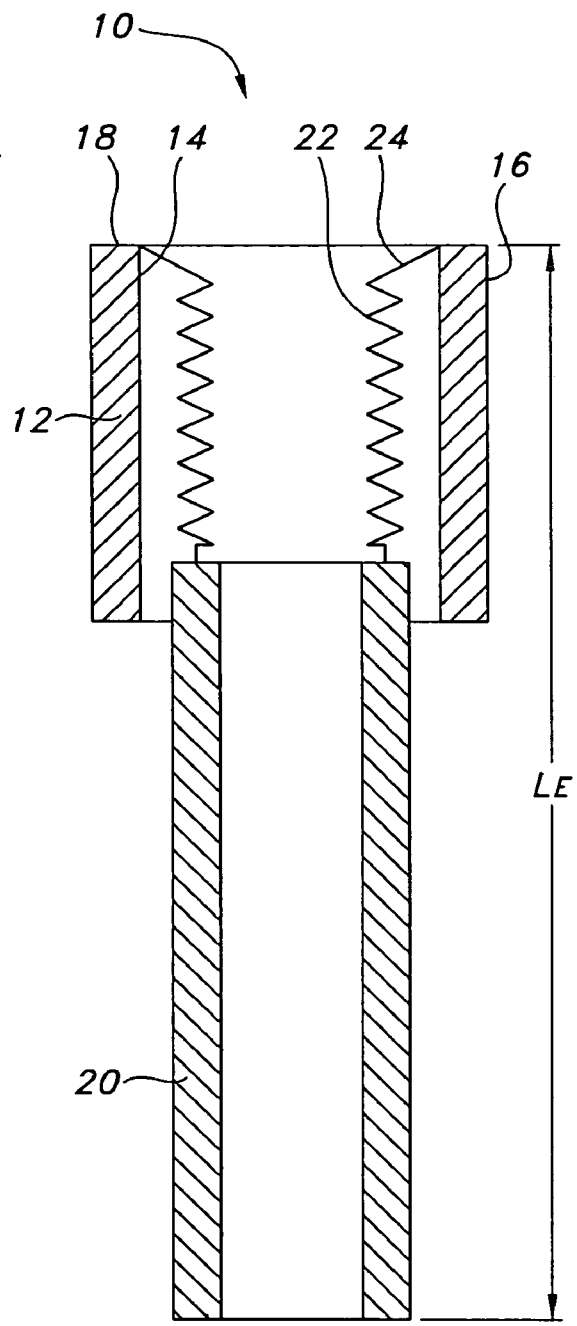
FIG. 1B is a cross-sectional view of the embodiment illustrated in FIG. 1A, showing the endovascular prosthesis in an expanded configuration.

Referring generally to FIGS. 1A and 1B, there is shown a variable length endovascular prosthesis 10 adapted to prevent endoleaks. Prosthesis 10 includes a substantially tubular first graft member 12 having an interior surface 14, an exterior surface 16, and a proximal end 18, and a substantially tubular second graft member 20 engaged coaxially within the first graft member 12. Prosthesis 10 further includes a substantially tubular fluid-tight connecting member 22 attached at one end to the first graft member 12 and attached at another end to the second graft member 20. Connecting member 22 is axially compressible and expandable to facilitate variable length engagement of the second graft member 20 within the first graft member 12 while maintaining a seal between the graft members 12, 20.

Connecting member 22 is formed from graft material of the second graft member 20 and is attached at a free end 24 to interior surface 14 of the first graft member 12. Free end 24 of connecting member 22 may be bonded to the first graft member 12 with an adhesive, e.g., Corethane®, or by any other means suitable for maintaining a fluid-tight seal. Connecting member 22 is pleated, and resides within the first graft member 12.

Various attachment configurations for connecting member 22 are contemplated. For example, connecting member 22 may be formed from graft material of the first graft member 12 and attached at a free end to the second graft member 20. Alternatively, connecting member 22 may be formed from a discrete segment of graft material, and attached at both free ends to the respective first and second graft members 12, 20. These alternative attachment configurations are not represented in the figures for clarity purposes.

FIG. 1A is a cross-sectional view of prosthesis 10 in a compressed configuration. More specifically, the pleats (also referred to as bellows) of connecting member 22 are compressed in an accordion-like fashion due to the coaxial positioning of the second graft member 20 relative to (and within) the first graft member 12, resulting in an axial length of prosthesis 10 of $L_C$. It is in this compressed configuration that prosthesis 10 is delivered to a desired location within a lumen.

The lumen within which prosthesis 10 is located typically undergoes a changing morphology, e.g., the lumen shrinks and/or kinks or straightens. The compressibility and expandability of connecting member 22 facilitates engagement of the second graft member 20 within the first graft member 12 to accommodate such a changing morphology, while maintaining a seal between the graft members 12, 20. In other words, in response to the changing morphology of the lumen, the graft members 12, 20 slide or telescope relative to one another, thereby varying the axial length of prosthesis 10.

FIG. 1B illustrates prosthesis 10 in an expanded configuration. More specifically, the pleats of connecting member 22 are expanded in an accordion-like fashion due to the coaxial positioning of the second graft member 20 relative to (and within) the first graft member 12, resulting in an axial length of prosthesis 10 of $L_E$. Because connecting member 22 is attached at one end to the first graft member 12 and attached at another end to the second graft member 20, a fluid-tight seal is maintained between the graft members 12, 20.

The representations of compressed axial length $L_C$ and expanded axial length $L_E$ in FIGS. 1A and 1B, respectively, are for illustrative purposes only. It is contemplated that the axial length of prosthesis 10 will vary, as necessary, to accommodate changing lumen morphology, constrained only by the compression and expansion limits of connecting member 22.

An exemplary material for forming graft members 12, 20 (and consequentially connecting member 22) is a synthetic polyester textile fiber. The present invention, however, is not limited to synthetic polyester textile fiber, and may include expanded polytetrafluoroethylene, or any other material that offers the desired fluid-tight sealing feature of connecting member 22.

Figures 2A, 2B:
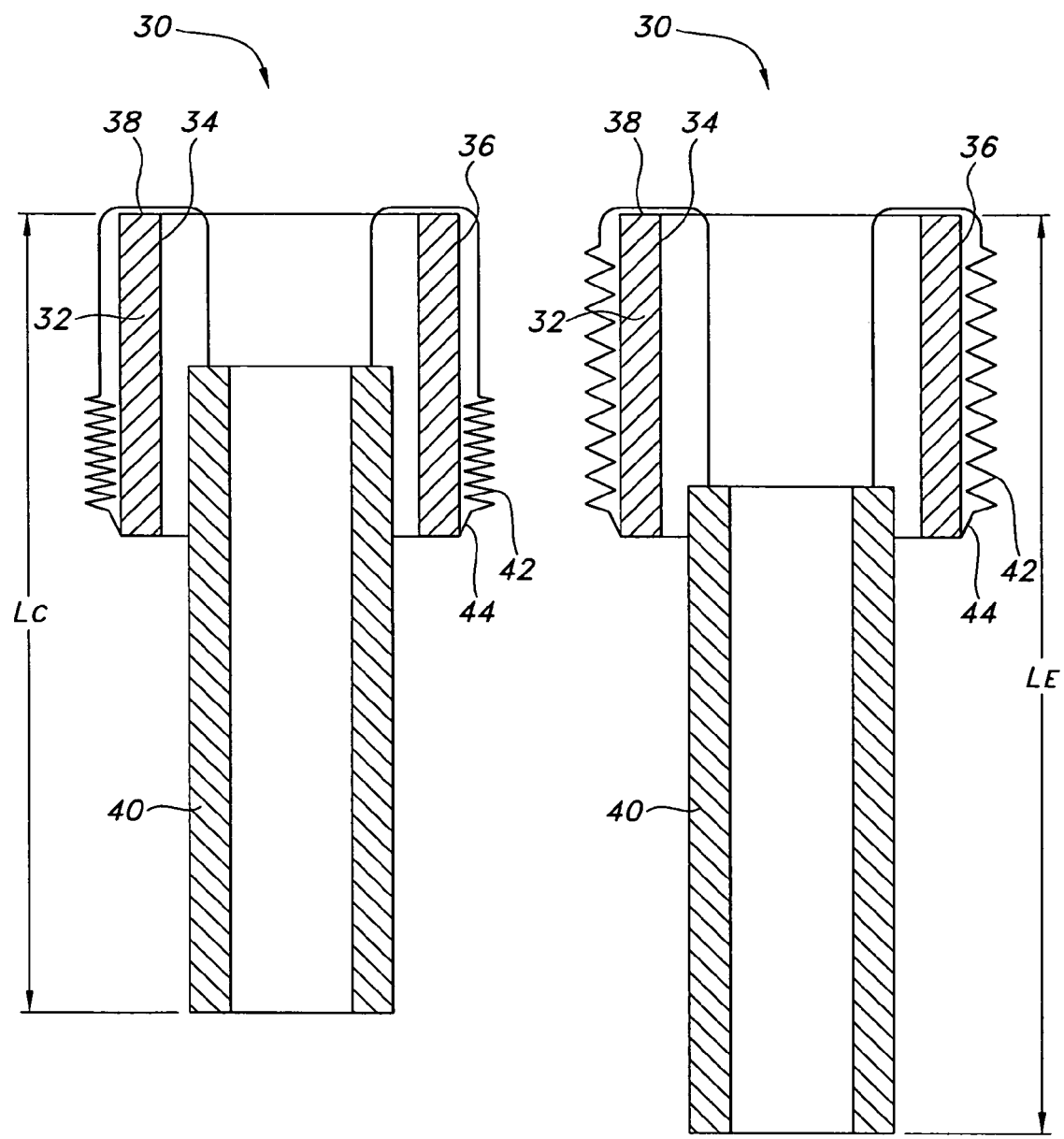
FIG. 2A is a cross-sectional view of another endovascular prosthesis in a compressed configuration, illustrating a pleated connecting member folded over a proximal end of a first graft member.
FIG. 2B is a cross-sectional view of the embodiment illustrated in FIG. 2A, showing the endovascular prosthesis in an expanded configuration.

FIGS. 2A and 2B illustrate another embodiment of a variable length endovascular prosthesis 30 adapted to prevent endoleaks. Similar to prosthesis 10 illustrated in FIGS. 1A and 1B, prosthesis 30 includes a substantially tubular first graft member 32 having an interior surface 34, an exterior surface 36, and a proximal end 38, and a substantially tubular second graft member 40 engaged coaxially within the first graft member 32. Prosthesis 30 further includes a substantially tubular fluid-tight connecting member 42 attached at one end to the first graft member 32 and attached at another end to the second graft member 40. Pleated connecting member 42 is axially compressible and expandable to facilitate engagement of the second graft member 40 within the first graft member 32 while maintaining a seal between the graft members 32, 40.

The configuration and operation of prosthesis 30 are essentially the same as those of prosthesis 10, described above with reference to FIGS. 1A and 1B. A notable difference, however, is the configuration of connecting member 42 in relation to the second graft member 40. More specifically, connecting member 42 is attached at a free end 44 to exterior surface 36 of the first graft member 32. As illustrated in FIGS. 2A and 2B, connecting member 42 folds over proximal end 38 of the first graft member 32.

FIG. 2A illustrates prosthesis 30 in a compressed configuration, and FIG. 2B illustrates prosthesis 30 in an expanded configuration.

Figure 3A:
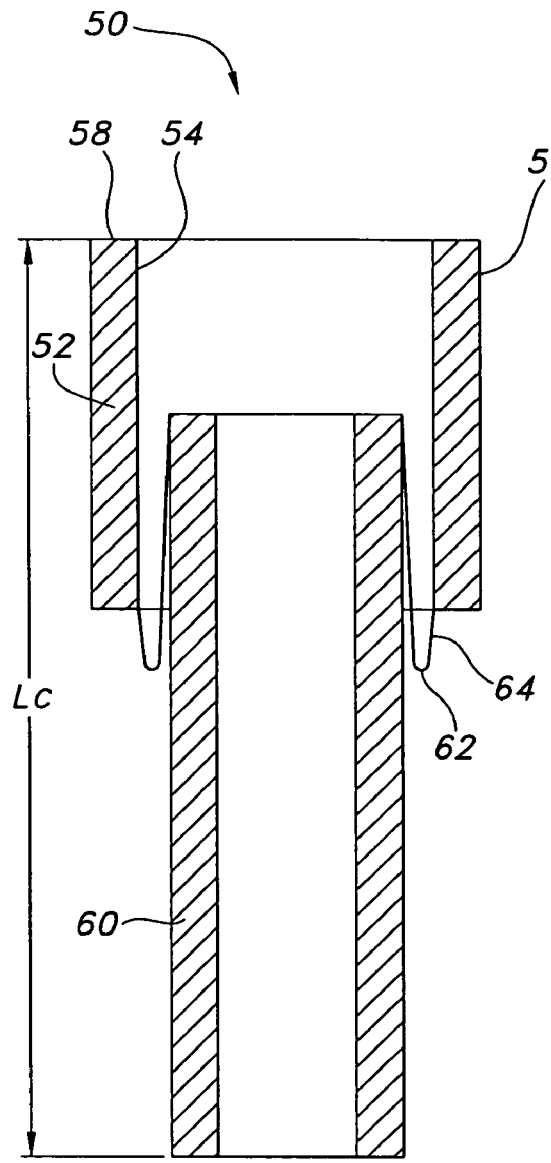
FIG. 3A is a cross-sectional view of yet another endovascular prosthesis in a compressed configuration, illustrating a substantially flat connecting member.
Figure 3B:
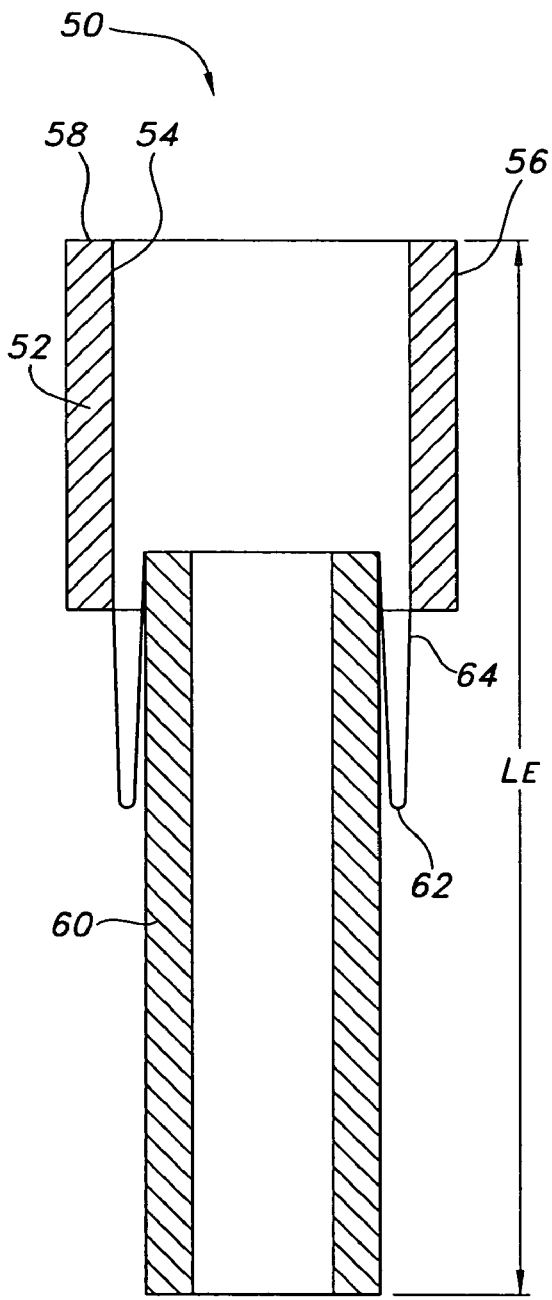
FIG. 3B is a cross-sectional view of the embodiment illustrated in FIG. 3A, showing the endovascular prosthesis in an expanded configuration.

FIGS. 3A and 3B illustrate yet another embodiment of a variable length endovascular prosthesis 50 adapted to prevent endoleaks. Similar to prosthesis 10 illustrated in FIGS. 1A and 1B, prosthesis 50 includes a substantially tubular first graft member 52 having an interior surface 54, an exterior surface 56, and a proximal end 58, and a substantially tubular second graft member 60 engaged coaxially within the first graft member 52. Prosthesis 50 further includes a substantially tubular fluid-tight connecting member 62 attached at one end to the first graft member 52 and attached at another end to the second graft member 60. Connecting member 62 is axially compressible and expandable to facilitate variable length of telescoping engagement of the second graft member 60 within the first graft member 52 while maintaining a seal between the graft members 52, 60.

The configuration and operation of prosthesis 50 are essentially the same as those of prosthesis 10, described above with reference to FIGS. 1A and 1B. A notable difference, however, is the shape of connecting member 62 and its configuration in relation to the second graft member 60. More specifically, connecting member 62 is substantially flat, and is attached at a free end 64 to interior surface 54 of the first graft member 52. As illustrated in FIGS. 3A and 3B, connecting member 62 hangs between the first and second graft members 52, 60.

FIG. 3A illustrates prosthesis 50 in a compressed configuration, and FIG. 3B illustrates prosthesis 50 in an expanded configuration.

The construction of variable length endovascular prostheses 10, 30, 50 is not limited to graft material. More specifically, prostheses 10, 30, 50 may include, for example, a substantially tubular first stent-graft 12, 32, 52, respectively, and a substantially tubular second stent-graft 20, 40, 60, respectively, engaged coaxially within first stent-graft 12, 32, 52, respectively. The endovascular prosthesis of the present invention may include two graft members constructed of graft material, two graft members constructed of stent-grafts, or a combination thereof.

The configuration and operation of these alternative embodiments are essentially the same as those described above with reference to FIGS. 1A-3B. The construction of the stents of stent-grafts 12, 20, 32, 40, 52, 60 may be of any type of self-expanding or balloon-expandable stent.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A variable length endovascular prosthesis adapted to prevent endoleaks, said prosthesis comprising:
    a substantially tubular first graft member comprising an interior surface, an exterior surface, and an open end;
    a substantially tubular second graft member engaged coaxially within said first graft member, the second graft member having a proximal end; and
    a substantially tubular fluid-tight connecting member attached at one end to said first graft member and attached at another end to said second graft member, wherein at least a portion of the connecting member is attached to the interior surface of the first graft member, with at least one end of the connecting member attached only to the interior surface,
    wherein said connecting member is axially compressible and expandable to facilitate engagement of said second graft member within said first graft member, such that a length of the endovascular prosthesis is variable while a particular length of the first graft member and a particular length of the second graft member is maintained, and while maintaining a seal between the proximal end of the second graft member and the open end of the first graft member and providing an opening between the first and second graft members at an opposing end of the first graft member.

2. The prosthesis of claim 1, wherein said connecting member comprises graft material.

3. The prosthesis of claim 1, wherein said connecting member is formed from graft material of said second graft member and is attached at a free end to said first graft member.

4. The prosthesis of claim 3, wherein said free end of said connecting member is attached to said interior surface of said first graft member.

5. The prosthesis of claim 4, wherein said connecting member resides within said first graft member.

6. The prosthesis of claim 1, wherein said first graft member comprises a first stent-graft.

7. The prosthesis of claim 1, wherein said second graft member comprises a second stent-graft.

8. The prosthesis of claim 1, wherein said first graft member comprises a first stent-graft, and said second graft member comprises a second stent-graft.

9. A variable length endovascular prosthesis adapted to prevent endoleaks, said prosthesis comprising:
    a substantially tubular first graft member comprising an interior surface, an exterior surface, and a proximal end;

a substantially tubular second graft member engaged coaxially within said first graft member; and a substantially tubular fluid-tight connecting member attached at one end to said first graft member and attached at another end to said second graft member wherein at least a portion of the connecting member is attached to the interior surface of the first graft member, with at least one end of the connecting member attached only to the interior surface, wherein said connecting member is axially compressible and expandable to facilitate engagement of said second graft member within said first graft member, such that a length of the endovascular prosthesis is variable while a particular length of the first graft member and a particular length of the second graft member is maintained, and while maintaining a seal between said graft members, wherein said connecting member is pleated.

10. A variable length endovascular prosthesis adapted to prevent endoleaks, said prosthesis comprising:

a substantially tubular first graft member having an open end and an interior surface;

a substantially tubular second graft member engaged coaxially within said first graft member, the second graft member having a proximal end; and a means for permitting axial compression and expansion of said prosthesis to facilitate variable length engagement of said second graft member within said first graft member, while a particular length of the first graft member and a particular length of the second graft member is maintained, and while maintaining a seal between the proximal end of the second graft member and the open end of the first graft member and providing an opening between the first and second graft members at an opposing end of the first graft member, wherein at least a portion of the means for permitting axial compression and expansion of said prosthesis is attached to the interior surface of the first graft member, with at least one end of the means for permitting axial compression and expansion of said prosthesis attached only to the interior surface.

11. The prosthesis of claim 10, wherein said means for axially compressing and expanding said prosthesis comprises a substantially tubular fluid-tight connecting member attached at one end to said first graft member and attached at another end to said second graft member.

12. A variable length endovascular prosthesis adapted to prevent endoleaks, said prosthesis comprising:

a first graft member comprising an interior surface, an exterior surface, and an open end;

a second graft member engaged coaxially within said first graft member, the second graft member having a proximal end; and a fluid-tight connecting member attached at one end to said first graft member and attached at another end to said second graft member, wherein at least a portion of the connecting member is attached to the interior surface of the first graft member, with at least one end of the connecting member attached only to the interior surface, wherein said connecting member is axially compressible and expandable to facilitate engagement of said second graft member within said first graft member, such that a length of the endovascular prosthesis is variable while a particular length of the first graft member and a particular length of the second graft member is maintained, and while maintaining a seal between the proximal end of the second graft member and the open end of the first graft member and providing an opening between the first and second graft members at an opposing end of the first graft member.

* * * * *